United States Patent
Bean (10) Patent No.: US 9,474,515 B2
(45) Date of Patent: Oct. 25, 2016

(54) ENDOSCOPIC HEMOSTASIS CLOSURE DEVICE AND DELIVERY SYSTEM

(75) Inventor: Jeffrey V. Bean, Fitchburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 988 days.

(21) Appl. No.: 13/592,788

(22) Filed: Aug. 23, 2012

(65) Prior Publication Data

US 2013/0066366 A1 Mar. 14, 2013

Related U.S. Application Data

(60) Provisional application No. 61/534,623, filed on Sep. 14, 2011.

(51) Int. Cl.
| | | |
|---|---|---|
| *A61B 17/22* | (2006.01) | |
| *A61B 17/00* | (2006.01) | |
| *A61B 17/068* | (2006.01) | |
| A61B 17/064 | (2006.01) | |
| A61B 1/018 | (2006.01) | |

(52) U.S. Cl.
CPC ......... *A61B 17/0057* (2013.01); *A61B 17/064* (2013.01); *A61B 17/068* (2013.01); *A61B 1/018* (2013.01); *A61B 17/0644* (2013.01); *A61B 2017/0061* (2013.01); *A61B 2017/00292* (2013.01); *A61B 2017/00579* (2013.01); *A61B 2017/00592* (2013.01); *A61B 2017/00623* (2013.01); *A61B 2017/00668* (2013.01); *A61B 2017/0641* (2013.01)

(58) Field of Classification Search
CPC .................................................. A61B 17/0057
USPC ................ 606/139, 142, 151, 157, 213, 219
See application file for complete search history.

(56) References Cited

U.S. PATENT DOCUMENTS

| | | | | |
|---|---|---|---|---|
| 5,478,353 | A | 12/1995 | Yoon | |
| 2005/0107809 | A1* | 5/2005 | Litscher | A61B 17/122 606/142 |
| 2009/0306681 | A1* | 12/2009 | Del Nido | A61B 17/0401 606/139 |

FOREIGN PATENT DOCUMENTS

WO 2007/089843 8/2007

* cited by examiner

*Primary Examiner* — Vy Bui
(74) *Attorney, Agent, or Firm* — Boston Scientific Scimed, Inc.

(57) ABSTRACT

A device for inserting a medical apparatus into a living body includes a handle and an elongated sheath extending from the handle to a distal end configured for insertion to a target location in the living body in combination with a clasp positioned within a distal portion of the elongated sheath and configured to temporarily attach to an endoscopic device and a spring retention mechanism movable from a first resting configuration maintaining a first closed position of the clasp to a second compressed configuration moving the clasp to an open position. A withdrawal mechanism is movable from a first resting configuration in which the distal end of the elongated sheath extends distally over a distal end of the endoscopic device to a second retracted configuration in which the distal end of the elongated sheath is moved proximally of the distal end of the endoscopic device.

14 Claims, 7 Drawing Sheets

ENDOSCOPIC HEMOSTASIS CLOSURE DEVICE AND DELIVERY SYSTEM

PRIORITY CLAIM

The application claims the priority to the U.S. Provisional Application Ser. No. 61/534,623, entitled "Endoscopic Hemostasis Closure Device and Delivery System" filed on Sep. 14, 2011. The specification of the above-identified application is incorporated herewith by reference.

BACKGROUND

Endoscopic procedures are vital in both the diagnosis and treatment of various medical conditions and diseases. Such procedures include, but are not limited to, surgeries, hemostasis procedures such as clipping, band ligation, injection therapy, thermal electrohemostasis and combination therapy. In these procedures, an endoscope is inserted to a target location within a living body and a delivery system including an endoscopic instrument is inserted through a working channel of the endoscope to carry the instrument to the target location. Each delivery system is generally adapted to deliver only one type of endoscopic instrument (e.g., a hemostatic clip) so the number of delivery systems required to perform a variety of procedures is virtually the same as the number of endoscopic instruments available to perform this range of procedures.

SUMMARY OF THE INVENTION

The present invention relates to a device for inserting a medical apparatus into a living body which includes a handle and an elongated sheath extending from the handle to a distal end configured for insertion to a target location in the living body in combination with a clasp positioned within a distal portion of the elongated sheath and configured to temporarily attach to an endoscopic device and a spring retention mechanism movable from a first resting configuration maintaining a first closed position of the clasp to a second compressed configuration moving the clasp to an open position. A withdrawal mechanism is movable from a first resting configuration in which the distal end of the elongated sheath extends distally over a distal end of the endoscopic device to a second retracted configuration in which the distal end of the elongated sheath is moved proximally of the distal end of the endoscopic device.

DETAILED DESCRIPTION

The present invention may be further understood with reference to the following description and the appended drawings, wherein like elements are referred to with the same reference numerals. The present invention relates to devices for performing a variety of endoscopic procedures including, but not limited to, clipping, band ligation, injection therapy, thermal electrohemostasis, combination therapy needle, biopsies and fine-needle aspiration. The exemplary delivery system according to the present invention is formed as an elongated device having a handle at a proximal end and a clasp at a distal end configured to house at least one custom endoscopic device therein. The clasp is controlled by a spring mechanism to permit a physician or other user to actuate the clasp to release the endoscopic device therefrom when desired, as will be described in greater detail below. The endoscopic device may be a hemostasis device configured to move from a compressed configuration within the clasp to a deployed expanded configuration to stop a flow of blood or other fluid in the target location, as will also be described in greater detail hereinafter. It should be noted that the terms "proximal" and "distal," as used herein, are intended to refer to a direct toward (proximal) and away from (distal) a user of the device.

Figure 1:
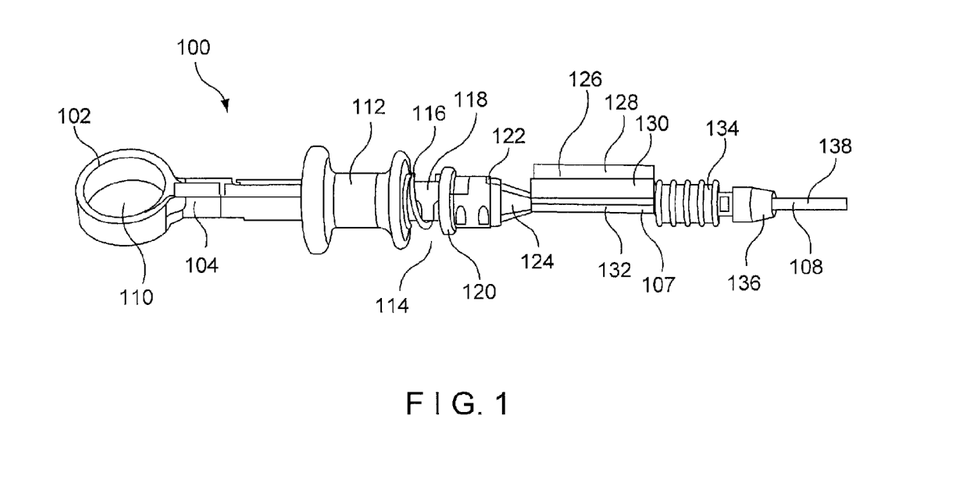
FIG. 1 shows a first perspective view of a device according to a first exemplary embodiment of the present invention in a first operative configuration.
Figure 2:
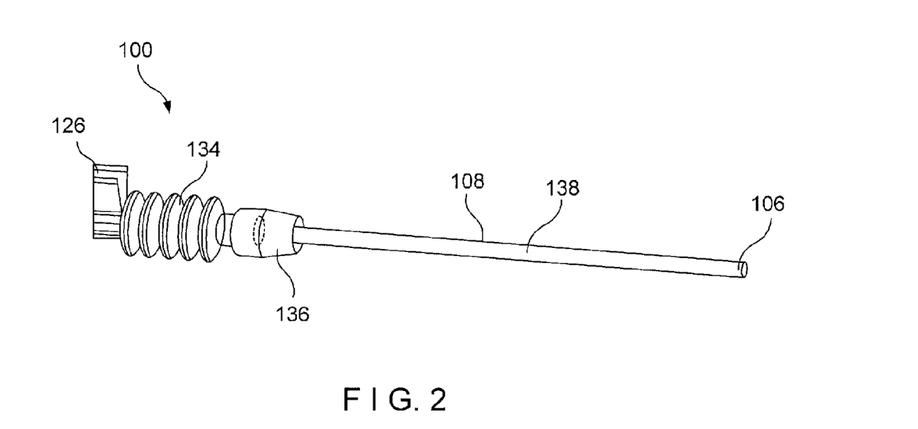
FIG. 2 shows a magnified view of the device of FIG. 1.

As shown in FIGS. 1-2, a device 100 according to a first exemplary embodiment of the invention extends longitudinally from a proximal end 102 comprising a handle 104 to a distal end 106 comprising an elongate flexible sheath 108. As would be understood by those skilled in the art, the device 100 may be formed of one of any of a variety of biocompatible materials including, for example, a plastic, a bio-absorbable material, coated metals and Nitinol. The handle 104 comprises a finger loop 110 and a spool 112 configured to aid in gripping and actuation of the device 100. A spring retention mechanism 114 is positioned distally of the handle 104 and may comprise a coil 116 wound over an elongated barrel 118. It is noted that although the present embodiment has been described with a coil 116, any spring may also be employed herein without deviating from the scope of the invention. In a first configuration, the coil 116 is compressed between the handle 104 and a radial abutment 120. An elongated cylinder 122 extends from the radial abutment 120 and may comprise a tapered portion 124 tapering down to a smaller diameter of an elongated portion 107 the diameter of which is made small enough to permit insertion thereof through the working channel of an endoscope while still housing a selected endoscopic device therewithin, as will be discussed in greater detail below. In another embodiment of the invention, the coil 116 may be omitted from the device 100.

The elongated portion 107 is fitted with a removable safety clip 126 formed as a jacket that may include first and second arms 128, 130 biased toward each other and enclosing an elongated groove 132. In an operative configuration, a physician or other used slides the safety clip 126 over the elongated portion 107 to temporarily separate the first and second arms 128, 130 from one another inserting the elongated portion 107 into the groove 132, as shown in FIG. 1. An accordioned sheath withdrawal mechanism 134 may be positioned distally of the safety clip 126 with a distal end of the withdrawal mechanism 134 connecting to a proximal end of an elongated sheath 108 via a coupler 136. The withdrawal mechanism 134 is prevented from moving proximally over the elongated portion 107 by engagement with the safety clip 126. In an exemplary embodiment, a length of the safety clip 126 is selected to be substantially equivalent to the combined length of a clasp 144 within a distal portion of the sheath 108 and an endoscopic device attached to the clasp 144, as will be discussed below. Specifically, the safety clip 126 is preferably dimensioned so that upon its removal from the device 100, proximal retraction of the elongated sheath 108 over the elongated portion 107 is permitted by a distance sufficient to expose the clasp 144 and an endoscopic device attached thereto from the distal end of the sheath 108. Specifically, an outer diameter of the elongated portion 107 is smaller than an inner diameter of the elongated sheath to permit the elongated sheath 108 to slide thereover when retracted. As shown in FIG. 2, in the resting configuration, the distal end 106 of the elongated sheath 108 extends distally over a distal end 216 of the first leg 204 of a hemostasis device 200 attached to the clasp 144, as will be described in greater detail later. The resting configuration is therefore suited to use during insertion of the elongated sheath 108 to a target location in the body and withdrawal of the device therefrom.

A lumen 138 extends through the length of the elongated sheath 108 with an elongated flexible clevis 140 extending therethrough. Specifically, a proximal portion (not shown) of the clevis 140 extending through the sheath 108 may be formed as a rod or wire. A proximal end (not shown) of the clevis 140 is operably connected to the spring retention mechanism 114 so that actuation of the spring retention mechanism 114 moves the clevis 140 within the controls operation of the clasp 144. Specifically, a distal end 142 of the clevis 140 is connected to the clasp 144 via a pivoting attachment comprising a pivot pin 146 inserted through a pivot hole 148 extending transversely through the first and second arms 150, 152 of the clasp 144. As those skilled in the art will understand, the pivoting attachment permits the first and second arms 150, 152 to move within a wide range of angles relative to one another. In an exemplary embodiment, the first and second arms 150, 152 may move up to 120° relative to one another although any other range of movement may be employed without deviating from the scope of the invention. Each of the arms 150, 152 is formed with a curved cross-sectional shape so that when the first and second arms 150, 152 are brought into a closed configuration (not shown), a hollow cavity 154 is defined therebetween. Specifically, each of the arms 150, 152 may be substantially concave to define the cavity 154 therebetween. Furthermore, although a substantially semi-circular shape is shown for each of the arms 150, 152, any other shape may be used without deviating from the spirit and scope of the invention. The curved shape of each of the aims 150, 152 also permits insertion of the clasp 144 through the hollow channel 138 while maximizing the size of the hollow cavity 154. However, as those skilled in the art will understand and as will be described in greater detail below, the cavity 154 may be made in any shape desired to grip a connecting part of an endoscopic device to be deployed thereby. For example, the cavity 154 may be configured to house one or more hemostasis devices 200, 300.

Each of the first and second arms 150, 152 comprises a slotted opening 154 extending therethrough configured to receive a tab 208 formed on the hemostasis device 200, as will be described in greater detail later. It is noted that although the present embodiment is depicted with a single opening 156 formed on each of the first and second arms 150, 152, the clasp 144 may alternately be formed with any number of openings on one or both of the first and second arms 150, 152 without deviating from the scope of the invention. The opening 156 may be formed of any shape without deviating from the scope of the invention (e.g., slotted, etc.). The number and position of the openings may be selected to conform to the tabs 208 provided on the hemostasis device 200.

Figure 4:
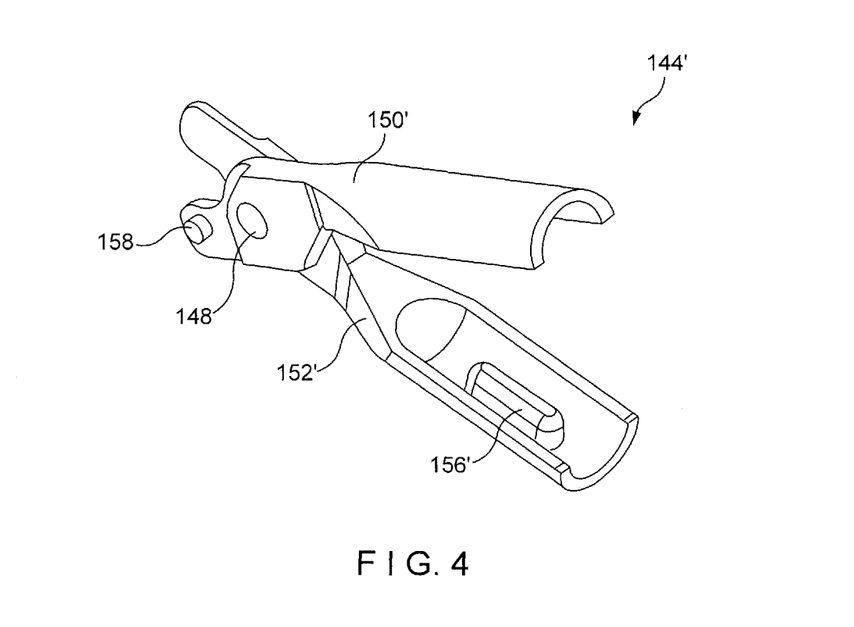
FIG. 4 shows a perspective view of a clasp according to a first alternate embodiment of the present invention.

FIG. 4 depicts a clasp 144' according to another embodiment of the invention. The clasp 144' is formed substantially similarly to the clasp 144 but does not comprise openings 156 extending through the first and second arms 150', 152'. Rather, the first and second arms 150', 152' are provided with tabs 156' configured to receive openings 308 formed on a hemostasis device 300. Each of the clasps 144, 144' comprises a pull wire attachment 158 provided on a proximal end of one or both of the first and second arms 150, 152 and 150', 152', respectively. The pull wire attachment 158 is connected to a wire (not shown) extending through the elongated sheath 108 to the spring mechanism 114 so that actuation of the spring mechanism causes the wire (not shown) to move the clasp 144, 144' to an open configuration. Specifically, actuation of the wire (not shown) permits the first arm 150, 150' to move pivotally away from the second arm 152, 152' about a pivot axis defined by the pivot pin 146. A user may actuate the spring mechanism 114 any plurality of times to move the clasp 144, 144' between the open and closed configurations.

In another embodiment of the invention (not shown), the clasp 144, 144' is provided with a snap and/or cartridge design to permit loading of any custom device thereonto. Specifically, while the present invention has been described with respect to a particular hemostasis device 200, those skilled in the art will understand that a variety of different endoscopic devices may be fitted to the clasp 144, 144' without deviating from the scope of the invention. The clasp 144, 144' may therefore be provided with any type of retention mechanism suitable to engage a desired device.

Figure 5:
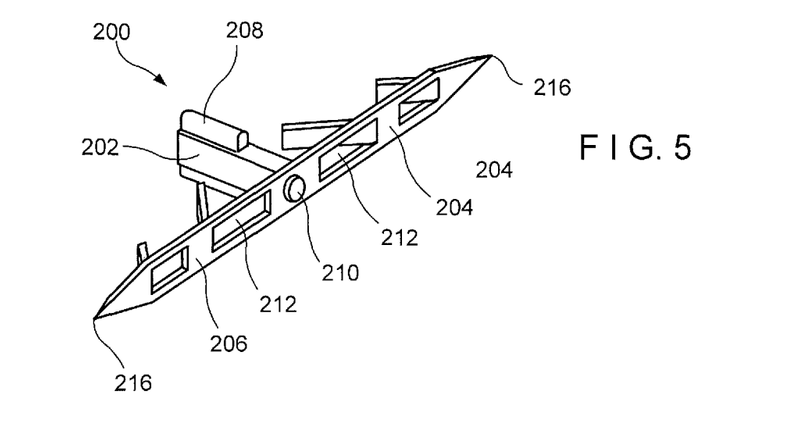
FIG. 5 shows a first perspective view of a hemostasis device according to a first exemplary embodiment of the present invention.
Figure 11:
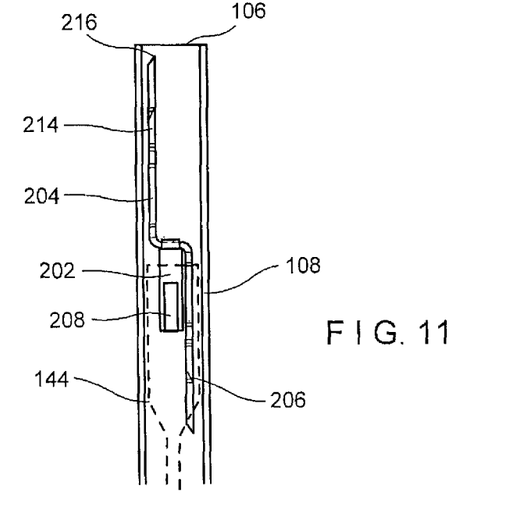
FIG. 11 shows a first partial cross-sectional view of a hemostasis device according to the present invention in a first operative configuration.

FIG. 5 depicts a first exemplary hemostasis closure device 200 according to the invention. The device 200 comprises a base portion 202 having first and second legs 204, 206 extending distally therefrom. In a first insertion configuration as shown in FIG. 11, the first and second legs 204, 206 extend substantially parallel to the base portion 202. Specifically, the first leg 204 is positioned to extend distally from the base portion 202 while the second leg 206 is positioned to extend proximally from the base portion 202. In an alternate embodiment (not shown), both of the first and second legs 204, 206 may be positioned to face either proximally or distally of the base portion 202.

The first and second legs 204, 206 are held in this insertion configuration within the elongated sheath 108 by frictional engagement with inner walls thereof as well as with inner walls of the first and second arms 150, 152 of the clasp 144. In another embodiment, the first and second legs 204, 206 may be held in the insertion configuration via a capsule (not shown) positioned therearound, as those skilled in the art will understand. The base portion 202 comprises at least one tab 208 extending therefrom configured to mate with the slotted opening 156 of the clasp 144, as described in greater detail earlier. The position of each of the one or more tabs 208 corresponds to a position of a corresponding one of the slotted openings 156. When inserted into the slotted openings 156, the tabs 208 hold the closure device 200 against the clasp 144 and aid in deploying and positioning the closure device 200 within the body, as will be described in greater detail later on. The first and second legs 204, 206 are connected to the base portion 202 via a joint 210 which may be a bolt, interference fit, snap fit or other attachment mechanism known in the art. It is further noted that although two legs 204, 206 are shown in the current embodiment to allow for a smaller profile during deployment of the closure device 200 in the body, any number of legs may be employed without deviating from the spirit and scope of the present invention.

Each of the first and second legs 204, 206 also comprises one or more cutouts 212 each defining a hook 214 extending proximally therefrom. In this embodiment, the cutouts 212 are substantially rectangular in shape and are formed via first, second and third cuts extending through the first and second legs 204, 206. It is noted however that the cutouts 212 may take any shape without deviating from the spirit and scope of the invention. Each hook portion 214 extends proximally away from a plane housing the corresponding cutout 212 angled at approximately 45° relative to the plane to form the hook portions 214 as proximally extending barbs. However, as would be understood by those skilled in the art, any other angle may be used without deviating from the scope of the present invention so long as the hook portions 214 are angled to operate as barbs to engage target tissue. Specifically, each hook 214 is biased to extend away from the plane housing the corresponding cutout 212 in a non-compressed configuration. When housed within the elongated sheath 108, however, restrictive forces applied by the inner wall of the elongated sheath 108 may move the hooks 214 to a compressed configuration in which the hooks 214 lie substantially flush with the planes of the corresponding cutouts 212, as shown in FIG. 11. It is further noted that although the present embodiment is depicted with two hooks 214 on each of the first and second legs 204, 206 any number of hooks 214 may be employed without deviating from the scope of the invention. Furthermore, the hooks 214 may alternatively be configured to extend distally from the first and second legs 204, 206. In an exemplary embodiment, the hooks 214 may be formed with varying sizes to aid in capturing tissue, as those skilled in the art will understand. A distal end of each of the first and second legs 204, 206 may come to a sharpened point 216 configured to aid in piercing and traversing past tissue, as those skilled in the art will understand.

Figure 6:
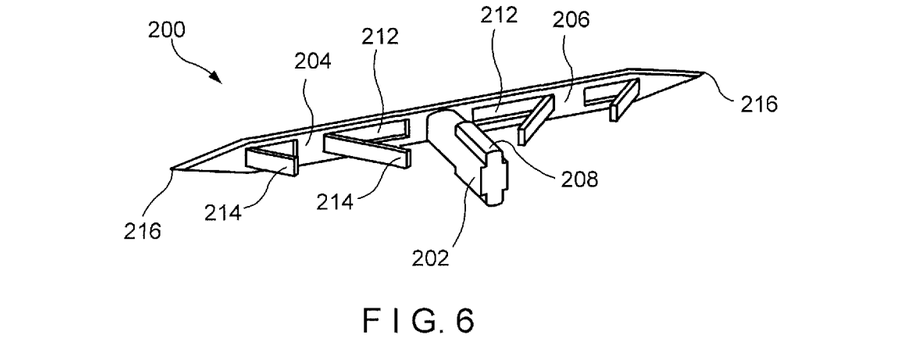
FIG. 6 shows a second perspective view of the hemostasis device of FIG. 5.
Figure 7:
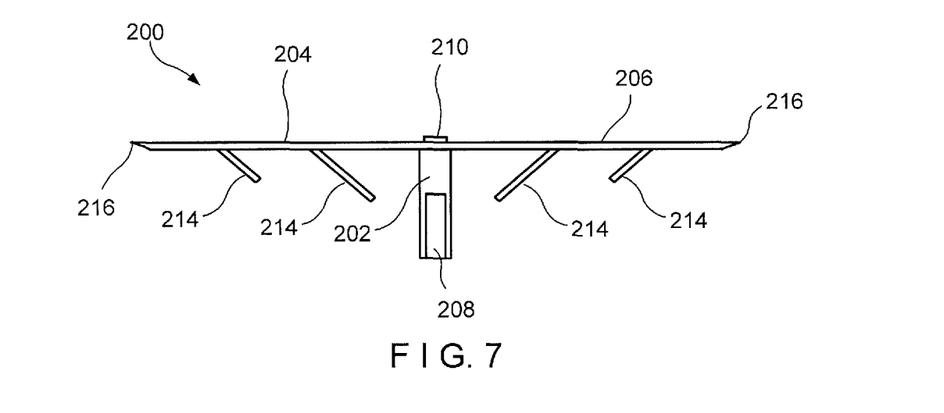
FIG. 7 shows a third perspective view of the hemostasis device of FIG. 5.
Figure 8:
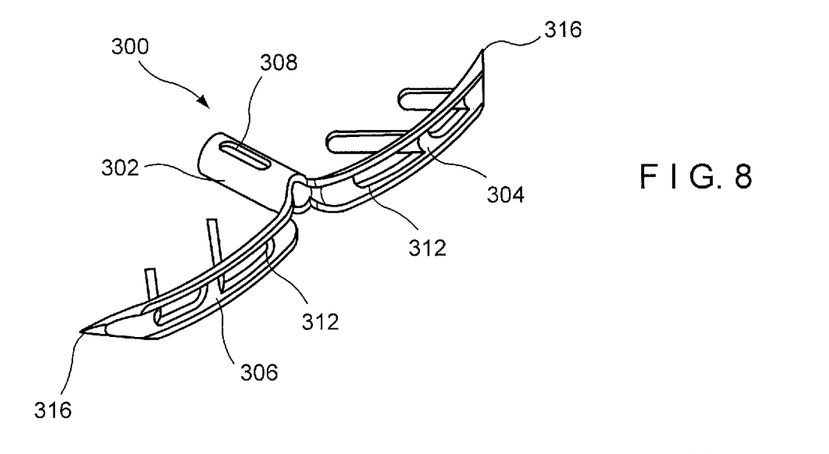
FIG. 8 shows a first perspective view of a hemostasis device according to a second exemplary embodiment of the present invention.
Figure 9:
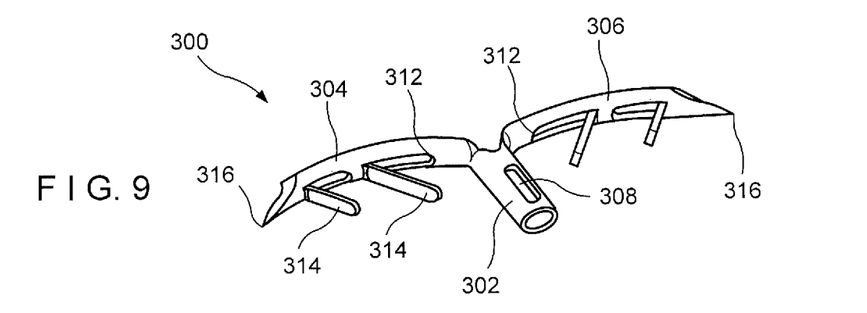
FIG. 9 shows a second perspective view of the hemostasis device of FIG. 8.
Figure 10:
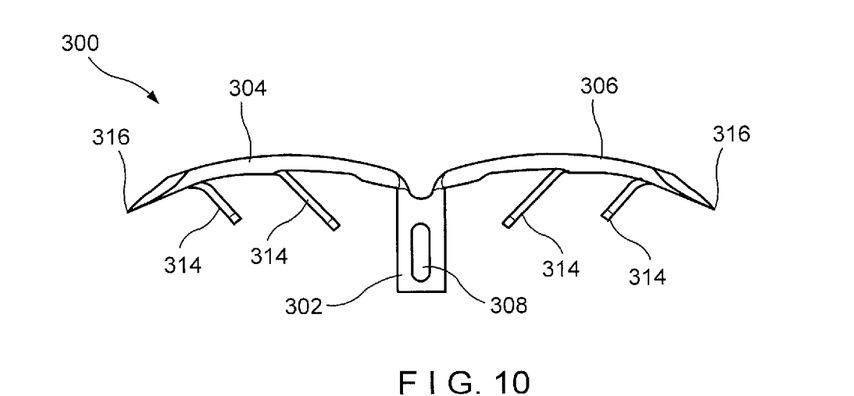
FIG. 10 shows a third perspective view of the hemostasis device of FIG. 8.

As shown in FIGS. 5-7, the first and second legs 204, 206 of the device 200 according to this embodiment are substantially planar. In another embodiment, as shown in FIGS. 8-10, the device 300 include first and second legs 304, 306 with a curved cross-sectional shape configured to aid in tissue retention, as those skilled in the art will understand. It is noted that although the legs 304, 306 are depicted as having a particular radius of curvature, any other radius of curvature may be employed without deviating from the scope of the invention. An exemplary radius of curvature of the first and second legs 304, 306 is selected in accordance with size limitations of the clasp 144' and the elongated sheath 108 as well as the requirements of a particular procedure to be performed in a living body, as those skilled in the art will understand. The closure device 300 is otherwise formed substantially similarly to the closure device 200, with first and second legs 304, 306 extending distally from a base portion 302. However, where the base portion 202 was connected to the first and second legs 204, 206 via a joint 210, the base portion 302 is formed integrally with the first and second legs 304, 306. Specifically, the base portion 302 is a hollow substantially cylindrical element having at least one opening 308 extending therethrough configured and dimensioned to receive the tab 156' of the clasp 144' of FIG. 4. The first and second legs 304, 306 also comprise openings 312 defining hooks 314 extending thereoutof at any selected angle as described above. Each of the first and second legs 304, 306 may terminate at a sharpened distal point 316. Furthermore, the legs 304, 306 may be provided with predetermined respective lengths, widths and thicknesses to affect performance thereof once implanted, as those skilled in the art will understand.

Figure 14:
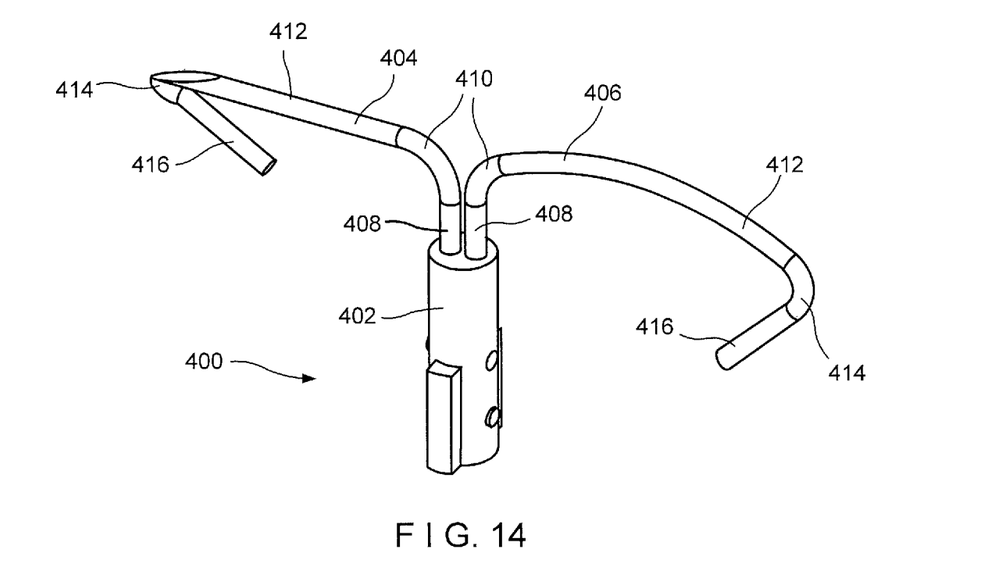
FIG. 14 shows a first perspective view of a clasp according to a second alternate embodiment of the present invention.
Figure 15:
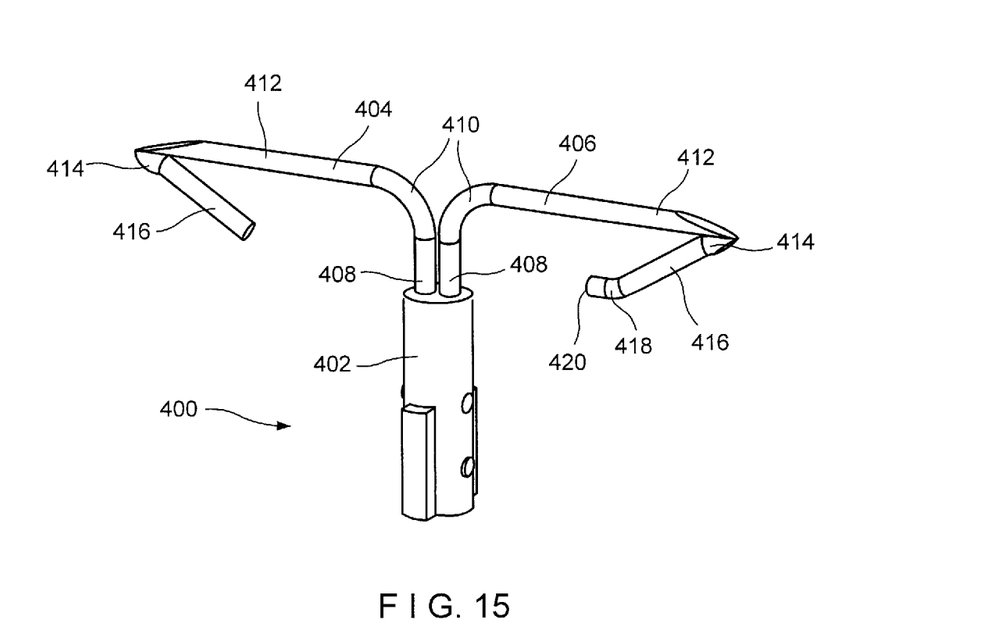
FIG. 15 shows a second perspective view of a clasp according to a second alternate embodiment of the present invention.

FIGS. 14-15 depict a hemostasis closure device 400 according to another embodiment of the invention. The device 400 is substantially similar to the device 300 of FIGS. 8-10 but is formed with a round-wire design. Specifically, the device 400 comprises a base portion 402 having first and second legs 404, 406 extending distally therefrom. The first and second legs 404, 406 may be formed of a solid wire or, in another embodiment, may be an extension of the wire (not shown) extending through the elongated sheath 108 to the handle 104, as discussed in greater detail earlier. The round wire design of the closure device 400 permits a wider range of curvature of the first and second legs 404, 406 while also preventing trauma to adjacent portions of tissue. In an insertion configuration (not shown), the first and second legs 404, 406 may assume a position substantially similar to that of closure devices 200, 300 as described in greater detail earlier. In an expanded configuration, each of the first and second legs 404, 406 extends at an angle relative to a longitudinal axis of the base portion 402. Each of the legs 404, 406 comprises a plurality of elongated portions 408, 410, 412, 414, 416 connected to one another. As would be understood by those skilled in the art, any number of elongated portions may be employed without deviating from the scope of the invention. Furthermore, each of the elongated portions 408, 410, 412, 414, 416 may be formed of any length suitable for a desired procedure. As those skilled in the art will understand, a longer length may be used if a larger radius of curvature is to be applied to a particular portion of the legs 404, 406 and a shorter length may be used if a smaller radius of curvature is to be applied. Accordingly, the lengths of each of the elongated portions 408, 410, 412, 414, 416 may be selected to permit the legs 404, 406 to conform to the anatomy of a target portion of tissue. Furthermore, a joint between each of the elongated portions 408, 410, 412, 414, 416 may function as a pivot point, permitting angling of each of the elongated portions 408, 410, 412, 414, 416 relative to one another at any angle. In one embodiment, each of the elongated portion 408, 410, 412, 414, 416 may be biased to have a predetermined radius of curvature and each of the joints between adjacent ones of the elongated portions 408, 410, 412, 414, 416 may be biased to permit adjacent ones of the elongated portions to be angled at a desired angle. For example, as shown in FIG. 14, the elongated portion 414 may be biased to an obtuse angle relative to the elongated portion 412. The first and second legs 404, 406 may each be formed with different numbers and lengths of elongated portions without deviating from the scope of the invention. As shown in FIG. 15, the second leg 406 may comprise additional elongated portions 418, 420 having a length and curvature suited to the requirements of a particular procedure.

Figure 16:
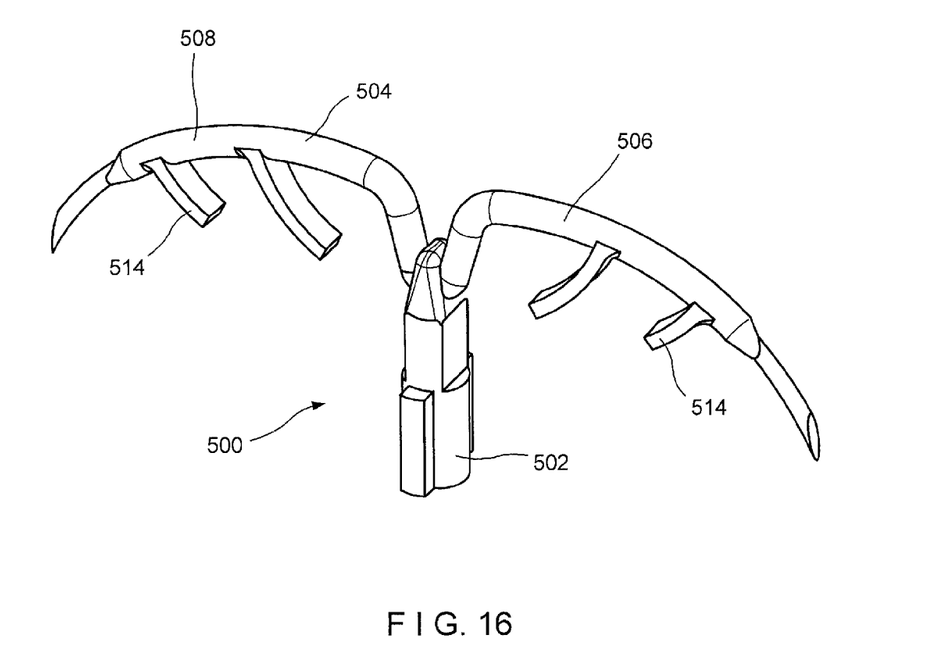
FIG. 16 shows a first perspective view of a clasp according to a third alternate embodiment of the present invention.
Figure 17:
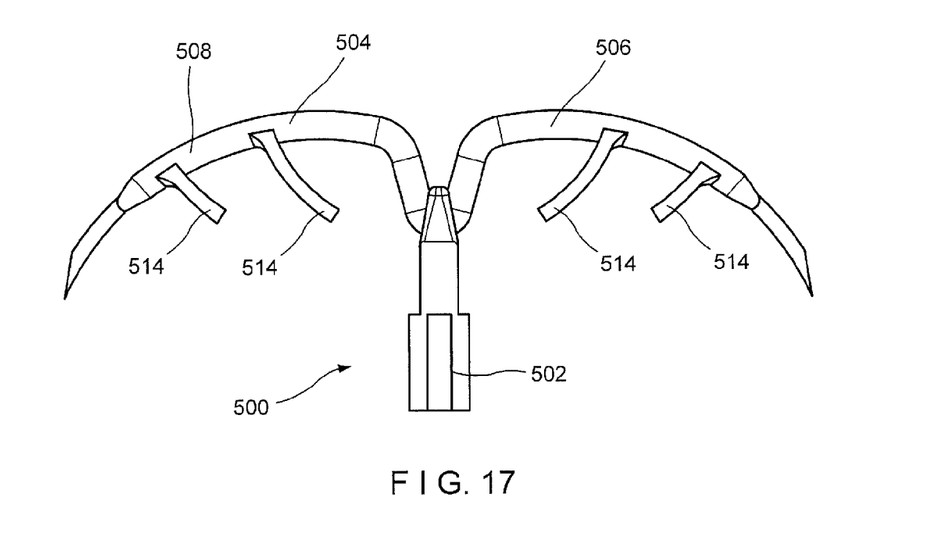
FIG. 17 shows a second perspective view of a clasp according to a third alternate embodiment of the present invention.

As shown in FIGS. 16-17, a closure device 500 according to another exemplary embodiment of the invention is substantially similar to the device 300 but is formed according to a round wire design. Specifically, the device 500 comprises first and second legs 504, 506 extending from a base portion 502. The legs 504, 506 are formed of a round wire having, for example, a substantially cylindrical shape. An overmold 508 provided over the first and second legs 504, 506 is formed of a plastic or other suitable material and includes barbs 514 extending therefrom. The barbs 514 may be formed substantially similar to the barbs 314 of the closure device 300. A curvature of the first and second legs 504, 506 is substantially similar to that of the closure device 300. The closure devices 200, 300, 400, 500 may be provided with first and second legs of different lengths selected to conform to the requirements of particular procedures. A position and number of the hooks and/or barbs may also be varied without deviating from the scope of the invention.

Figure 12:
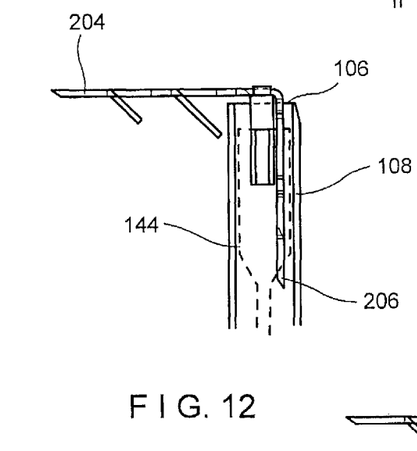
FIG. 12 shows a second partial cross-sectional view of the hemostasis device of FIG. 11 in a second operative configuration.
Figure 13:
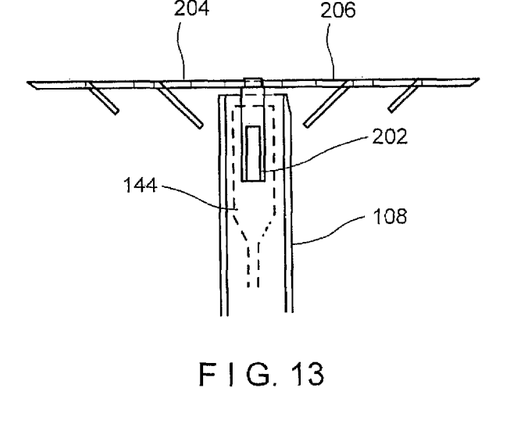
FIG. 13 shows a third partial cross-sectional view of the hemostasis device of FIG. 11 in a third operative configuration.

FIGS. 11-13 depict an exemplary method of operating the device 100 according to the present invention. The device 100 is initially loaded within the sheath 108 with the first leg 204 extending distally from the clasp 144 toward the distal end 106 of the elongated sheath 108 while the second leg 206 extends proximally from the clasp 144. In this position, the elongated sheath 108 is guided to a target position within a living body, for example, by passing the sheath 108 through the working channel of an endoscope. In the insertion configuration, the clasp 144 is maintained in the closed position via compressive force applied by the spring retention mechanism 114. The distal end 106 of the sheath 108 is extended distally from the end of the endoscope and passed through a wound or surgical opening to be closed. At this point, the user removes the safety clip 126 from the device 100. A physician or other user then applies a proximally directed force to the withdrawal mechanism 134 to move the elongated sheath 108 proximally relative to the clasp 144 and closure device 200. As the elongated sheath 108 moves proximally and the first leg 204 extends distally from the sheath 108, the compressive force applied to the first leg 204 by the sheath 108 is removed, allowing the first leg 204 to rotate under its natural bias until it extends transverse to a longitudinal axis of the elongated sheath 108 (in this embodiment, substantially perpendicularly to the axis), as shown in FIG. 12. In an alternate embodiment, each of the first and second legs 204, 206 may be biased to extend away from the compressed insertion configuration by an angle greater than 90° so that, upon deployment, the first and second legs 204, 206 can pinch and/or apply a greater holding force to the target tissue, as those skilled in the art will understand. This rotation causes the first leg 104 and the hooks 214 to engage the tissue on one side of the opening to be closed with the angulation of the hooks 214 drawing the tissue toward the clasp 144. The exemplary first and second legs 204, 206 according to the invention may be deployed in any other way without deviating from the scope of the invention as long as the first and second legs 204, 206 maintain a low profile during insertion and a extend to a high profile when deployed. For example, in one embodiment (not shown), the first and second legs 204, 206 may be folded in on themselves during insertion and may unfold upon proximal retraction of the elongated sheath 108. Specifically, the first and second legs 204, 206 may each be formed with one or more fold lines defining folding positions thereof when received within the elongated sheath 108. In another embodiment, the first and second legs 204, 206 may be wrapped (e.g., helically, etc.) about one another or about the elongated sheath 108 and may unfurl upon deployment.

The distal end 106 of the sheath 108 is then angled relative to the opening and the sheath 108 is moved further through the opening until the outer end of the second leg 206 within the sheath 108 extends through the opening. At this point, the elongated sheath 108 is withdrawn further proximally to expose the second leg 206 which now rotates under its natural bias to extend transverse to the longitudinal axis of the elongated sheath 108, as shown in FIG. 13. The user then draws the sheath 108 to fully expose the clevis 140 proximally to bring the hooks 214 of the second arm 206 into engagement with the tissue, drawing the opening closed around the clasp 144 closing the opening. Further proximal retraction of the elongated sheath via the withdrawal mechanism 134 exposes the clasp 144 and the tab 208. Specifically, the safety clip 126 is configured and dimensioned so that when the withdrawal mechanism 134 is moved to a proximal-most position, the clasp 144 is positioned distally of the distal end 106 of the elongated sheath 108.

Figure 3:
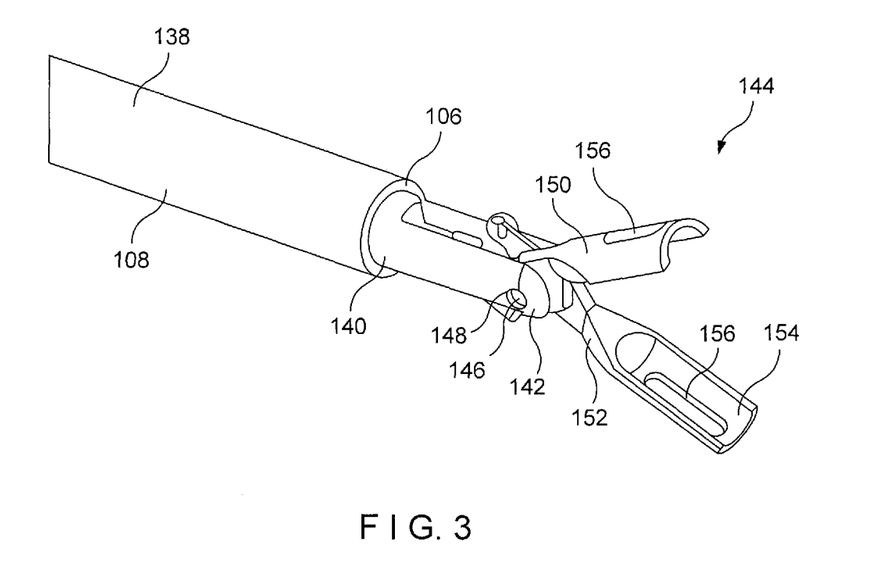
FIG. 3 shows a perspective view of the device of FIG. 1 in a second operative configuration.

The elongated cylinder 122 is then moved proximally to longitudinally compress the spring mechanism 114, the compression causing an actuation of the wire (not shown) extending from a proximal end of the device 100, through the elongated sheath 108 to the pull wire attachment 158 of the clasp 144. This actuation causes the wire (not shown) to pull proximally on a tang of the clasp 144 and move the clasp to the open configuration of FIG. 3 with the first arm 150 pivoted away from the second arm 152 about the pivot pin 146. This movement causes the tabs 208 of the closure device 200 to disengage from the slotted openings 156, separating the closure device 200 from the device 100. The clevis 140 is then withdrawn proximally to draw the clasp 144 into the sheath 108 and the device 100 is then withdrawn from the body. The elongated sheath 108 may be moved distally to cover the clasp 144 and the entire device 100 may be removed from the body. In another embodiment of the invention, one or more additional closure devices 200 may be inserted to the target region in accordance with the requirements of a particular procedure, as those skilled in the art will understand. For example, the device 100 may be withdrawn from the body and a second closure device 200 may be coupled to the clasp 144 and loaded into the sheath 108. The user may then apply this second closure in the same manner indicated above.

The exemplary device according to the present invention may be particularly useful in stopping bleeding within the mucosal and serosal layers of the stomach where clipping via presently available systems and methods has often been ineffective in stopping blood from exiting the serosal side. Specifically, the endoscope is inserted into the stomach and the sheath 108 is extended through an opening out of the stomach so that the hooks 214 of the first and second legs 204, 206 engage the submucosal layer as described above to close and seal the opening in the stomach wall. Furthermore, the device may be deployed from one of within and outside a body organ so position the closure devices one of within and outside of the organ, respectively.

It will be understood by those of skill in the art that individual features of the embodiments described above may be omitted and or combined to form alternate embodiments. The components of the exemplary system according to the invention may be formed of one or more of Nitinol, stainless steel, elgiloy, polymers, biocompatible materials and combination of the above. Furthermore, it will be understood by those skilled in the art that various modification can be made in the structure and the methodology of the present invention, without departing from the spirit or scope of the invention. For example, the exemplary closure device 200 according to the invention may be guided and actuated by a device other than the clasp 144. In one such embodiment (not shown), the closure device 200 may be attached to a wire (not shown) having a frangible connection configured to fracture upon actuation by a user, as described in greater detail earlier. In such an embodiment, the closure device 200 may omit the tabs 208. Rather, the closure device 200 may be attached to the wire (not shown) by one of an adhesive, weld, hook, interference fit, etc., as those skilled in the art will understand.

Thus, it is intended that the present invention cover the modifications and variations of this invention provided that they come within the scope of the appended claims and their equivalents.

What is claimed is:

1. A medical device, comprising:
    a clasp configured to be positioned within a distal portion of an endoscopic device, the clasp comprising first and second arms configured to be movable from a closed configuration to an open configuration in which the first and second arms are pivoted away from one another over a pivot point positioned adjacent a proximal end of the clasp; and
    a hemostasis device having first and second legs extending from a base portion removably attached to the clasp, each of the first and second legs comprising a hook extending therefrom and configured to enter target tissue and draw the target tissue toward the base portion,
    wherein, in a closed configuration within the endoscopic device, the first leg extends proximally from the base portion and the second leg extends distally from the base portion.

2. The device of claim 1, wherein the hemostasis device is biased to an open configuration in which each of the first and second legs extends transverse to a longitudinal axis of the base portion and is held in the closed configuration when located within the endoscopic device by a compressive force applied thereto by the endoscopic device.

3. The device of claim 2, wherein the hemostasis device comprises a tab configured to engage a corresponding slot in the clasp to permit engagement therewith, disengagement of the tab from the slot deploying the hemostasis device in the living body.

4. The device of claim 2, wherein, in the closed configuration, the first and second legs are one of wound around one another, wound around a portion of the endoscopic device and folded.

5. The device of claim 2, wherein the first leg extends from a first side of the base portion and the second leg extends from a second side of the base portion opposite the first side.

6. The device of claim 5, wherein, when the hemostasis device is detached from the clasp, the first leg moves to the open configuration prior to the second leg moving to the open configuration.

7. The device of claim 1, wherein the hook in the first leg extends at an angle relative to a plane housing the first leg and the hook in the second leg extends at an angle relative to a plane housing the second leg.

8. The device of claim 1, wherein the first and second legs are arcuate.

9. The device of claim 1, wherein first and second ends of the first and second legs are pointed.

10. The device of claim 1, wherein the first and second arms of the clasp comprise substantially concave shapes such that, when the clasp is in the closed configuration, a cavity is defined between the first and second arms.

11. The device of claim 1, further comprising:
    a delivery device configured to guide insertion of the hemostasis device to target location in a living body, the delivery device comprising a handle and an elongated sheath extending from the handle to a distal end configured for insertion to a target location in the living body, and a withdrawal mechanism movable from a first resting configuration in which the distal end of the elongated sheath extends distally over a distal end of the endoscopic device to a second retracted configuration in which the distal end of the elongated sheath is moved proximally of the distal end of the endoscopic device.

12. The device of claim 11, wherein the delivery device further comprises a spring retention mechanism movable from a first resting configuration maintaining a first closed position of the clasp to a second compressed configuration moving the clasp to an open position.

13. The device of claim 12, further comprising:
    a wire extending through the elongated sheath from the spring retention mechanism to a proximal end of the endoscopic device, the wire being actuatable by the spring retention mechanism.

14. The device of claim 11, further comprising:
    a safety clip positioned proximally of the withdrawal mechanism and configured to lock the withdrawal mechanism in the first resting configuration, removal of the safety clip from the device permitting movement of the withdrawal mechanism to the second retracted configuration.

* * * * *